United States Patent
Hopkins

(10) Patent No.: US 11,464,644 B2
(45) Date of Patent: Oct. 11, 2022

(54) METHOD FOR MULTI-CURVATURE LINERS FOR REVERSED SHOULDER REPLACEMENT

(71) Applicant: Zimmer, Inc., Warsaw, IN (US)

(72) Inventor: Andrew Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 69 days.

(21) Appl. No.: 16/832,548

(22) Filed: Mar. 27, 2020

(65) Prior Publication Data
US 2020/0222199 A1    Jul. 16, 2020

Related U.S. Application Data

(62) Division of application No. 15/367,881, filed on Dec. 2, 2016, now Pat. No. 10,631,992.

(60) Provisional application No. 62/262,415, filed on Dec. 3, 2015.

(51) Int. Cl.
*A61F 2/40* (2006.01)
*A61F 2/30* (2006.01)
*A61F 2/34* (2006.01)

(52) U.S. Cl.
CPC ........ *A61F 2/4003* (2013.01); *A61F 2/30724* (2013.01); *A61F 2/40* (2013.01); *A61F 2/4014* (2013.01); *A61F 2/4059* (2013.01); *A61F 2/4081* (2013.01); *A61F 2/34* (2013.01); *A61F 2002/3055* (2013.01); *A61F 2002/3066* (2013.01); *A61F 2002/30332* (2013.01); *A61F 2002/30604* (2013.01); *A61F 2002/30657* (2013.01); *A61F 2002/30658* (2013.01); *A61F 2002/30934* (2013.01); *A61F 2002/30935* (2013.01); *A61F 2002/4022* (2013.01); *A61F 2002/4085* (2013.01)

(58) Field of Classification Search
CPC ....... A61F 2/40–4081; A61F 2/32; A61F 2/34
See application file for complete search history.

(56) References Cited

U.S. PATENT DOCUMENTS

| | | |
|---|---|---|
| 4,784,662 A | 11/1988 | Muller |
| 2006/0069445 A1 | 3/2006 | Ondrla et al. |
| 2007/0173945 A1 | 7/2007 | Wiley et al. |
| 2007/0225818 A1 | 9/2007 | Reubelt et al. |
| 2009/0192621 A1 | 7/2009 | Winslow et al. |
| 2010/0063589 A1 | 3/2010 | Tepic |
| 2011/0276144 A1 | 11/2011 | Wirth et al. |
| 2013/0204375 A1 | 8/2013 | Winslow et al. |
| 2017/0156873 A1 | 6/2017 | Hopkins |

OTHER PUBLICATIONS

"U.S. Appl. No. 15/367,881, Examiner Interview Summary dated Aug. 13, 2019", 4 pgs.
"U.S. Appl. No. 15/367,881, Final Office Action dated Jun. 25, 2019", 17 pgs.

(Continued)

*Primary Examiner* — Marcia L Watkins
(74) *Attorney, Agent, or Firm* — Schwegman Lundberg & Woessner, P.A.

(57) ABSTRACT

A reverse shoulder replacement system including a humeral liner defining a split curvature bearing surface that includes a plurality of curvature regions. The plurality of curvature regions are configured to engage a glenosphere of a glenoid implant individually or in combination to provide an improved fit between the glenosphere and the humeral liner.

20 Claims, 3 Drawing Sheets

(56) References Cited

OTHER PUBLICATIONS

"U.S. Appl. No. 15/367,881, Non Final Office Action dated Feb. 4, 2019", 14 pgs.
"U.S. Appl. No. 15/367,881, Notice of Allowance dated Dec. 30, 2019", 10 pgs.
"U.S. Appl. No. 15/367,881, Response filed May 6, 19 to Non Final Office Action dated Feb. 4, 2019", 15 pgs.
"U.S. Appl. No. 15/367,881, Response filed Jun. 27, 2018 to Restriction Requirement Action dated Jun. 8, 2018", 6 pgs.
"U.S. Appl. No. 15/367,881, Response Filed Oct. 29, 2018 to Restriction Requirement Filed Aug. 27, 2018", 7 pgs.
"U.S. Appl. No. 15/367,881, Response filed Sep. 4, 2019 to Final Office Action dated Jun. 25, 2019", 18 pgs.
"U.S. Appl. No. 15/367,881, Restriction Requirement dated Jun. 8, 2018", 6 pgs.
"U.S. Appl. No. 15/367,881, Restriction Requirement dated Aug. 27, 2018", 6 pgs.
"European Application Serial No. 16202061.4, Communication Pursuant to Article 94(3) EPC dated Jun. 6, 2018", 3 pgs.
"European Application Serial No. 16202061.4, Extended European Search Report dated May 12, 2017", 8 pgs.
"European Application Serial No. 16202061.4, Response filed Dec. 14, 2017 to Extended European Search Report dated May 12, 2017", 15 pgs.
"Operative Technique Brochure", Equinoxe, (2007), 14 pgs.

METHOD FOR MULTI-CURVATURE LINERS FOR REVERSED SHOULDER REPLACEMENT

CLAIM OF PRIORITY

This patent application is a divisional of U.S. patent application Ser. No. 15/367,881, filed on Dec. 2, 2016, which claims the benefit of priority, under 35 U.S.C. Section 119(e), to Andrew Hopkins, U.S. Patent Application Ser. No. 62/262,415, entitled "MULTI-CURVATURE LINERS FOR REVERSED SHOULDER REPLACEMENT," filed on Dec. 3, 2015, which is hereby incorporated by reference herein in its entirety.

TECHNICAL FIELD

The document pertains generally, but not by way of limitation, to systems and related methods for reversed shoulder replacement procedures.

BACKGROUND

The shoulder joint is formed by the ball-shaped humeral head of the humerus rotatably being received within the glenoid cavity of the scapula. A group of tendons and muscles at the rotator cuff extend between the scapula and the humerus to maintain the humeral head within the glenoid cavity. Disease and overuse can cause the rotator cuff muscles and tendons to become damaged, weakening the connection between the humeral head and the glenoid cavity and permitting the humeral head to shift or track unnaturally within the glenoid cavity. The irregular movement of the humeral head can damage the humeral head or the scapula, requiring repair or replacement of the humeral head or the bone surrounding the glenoid cavity.

In conventional shoulder replacement procedures, a humeral implant having a ball head and/or a glenoid implant defining a socket are mounted to the humerus and scapula, respectively. The conventional humeral and glenoid implants are intended to supplement or replace the existing bone structure damaged by the irregular movement of the humeral head. As the conventional implants are substitutes for the natural structures, conventional shoulder replacement procedures require the rotator cuff muscles and tendons to be sufficiently undamaged or healed to maintain proper contact between the humeral head and glenoid cavity and prevent irregular movement of the humeral head.

A reverse shoulder replacement procedure can be employed if the rotator cuff muscles and tendons are too damaged for a conventional procedure. In reverse shoulder replacement, a glenoid implant having a ball head, or glenosphere, can be mounted to the scapula and a humeral implant defining a socket is mounted to the humerus. The glenoid and humeral implants reverse the ball and socket of the natural shoulder joint such that the deltoid muscle, rather than the damaged rotator cuff muscles and tendons, can be used to maintain the joining of the humerus and scapular.

Overview

The present inventors have recognized, among other things, that a problem to be solved can include that in modular reverse shoulder systems, the glenosphere of the selected glenoid implant must be correctly matched with the humeral implant defining a socket of the appropriate curvature. As reverse shoulder replacement procedures reverse the normal orientation of the shoulder, the fit of the glenosphere of the glenoid implant to the socket defined by the humeral implant can significantly impact the resulting joint tension. Reverse shoulder implant systems can be modular systems including a plurality of glenospheres of different diameters and a plurality of different humeral implants each including a socket of a different curvature to assist surgeons in providing the proper fit. Surgeons select the appropriate glenosphere diameter based on the dimensions of the scapula, the orientation of the glenoid cavity, the desired joint angle, and other factors. Surgeons then select the appropriate curvature of the socket defined by the humeral implant that corresponds to the diameter of the glenosphere and other physical constraints of the reversed joint.

However, if the surgeon incorrectly selects the glenoid cavity curvature or glenosphere diameter, the joint contact can be insufficiently tight causing excessive wear of the joint and/or damage to the joint thereby requiring revision surgery. In an example, the present subject matter can provide a solution to this problem, such as providing a humeral implant configured to receive a humeral liner defining a split curvature bearing surface. The split curvature bearing surface can include two or more curvature regions, each curvature region having a different curvature for engaging a glenosphere of a glenoid implant. The different curvature region can permit a single humeral implant to interface with glenospheres of different diameters and can account for different joint angles. This arrangement can reduce the likelihood of a mismatch between the humeral implant and the selected glenoid implant thereby reducing a likelihood that revision surgery will be required. The split curvature also can account for slight mismatches between the curvature regions of the humeral liner and the glenosphere by providing a series of regions of different curvatures reducing the potential differences between curvature and glenosphere diameters. This arrangement can also help reduce the complexity and cost of the implant procedure as only multiple glenoid implants need be provided for selection instead of providing both multiple humeral implants and glenoid implants.

In an example, the curvature regions of the split curvature bearing surface can be configured to facilitate wearing in or "bedding" of the split curvature bearing surface by the glenosphere through repeated use of the assembled joint. In at least one example, the flatter curvature regions can be positioned proximate the center of the split curvature bearing surface while the steeper curvature regions can be positioned proximate the edges of the split curvature bearing surface. The wearing in of the split curvature bearing surface can erode a portion of the slightly mismatched curvature regions and/or the interface between curvature regions such as to improve the fit of the glenosphere to the humeral liner thereby providing flexibility in the selection of the humeral liner. The split curvature bearing surface can be configured to deflect or deform to conform the split curvature bearing surface to the glenosphere. The wearing-in of the split-curvature bearing surface can improve the fit of the humeral implant to the selected glenoid implant. In at least one example, the humeral liner can comprise a deformable biocompatible material, such as polyethylene, which can facilitate wear or deflection of the split curvature bearing surface such as to correspond to the glenosphere over time.

A reverse shoulder replacement system, according to an example of the present disclosure, can include a humeral liner defining a split curvature bearing surface. The split curvature bearing surface can include a plurality of curvature regions, such as can include at least a first curvature region having a first curvature, and a second curvature region having a second curvature. The first curvature can be defined by a first radius extending from a first focal point, while the second curvature can be defined by a second radius extending from a second focal point. In an example, the first radius is shorter than the second radius such that the second curvature is shallower than the first curvature. In at least one example, the humeral liner can comprise a biocompatible deformable material, such as polyethylene.

A method for reverse shoulder replacement, according to an example of the present disclosure can include inserting a stem of a humeral implant into a humerus and mounting a humeral liner to an end of the stem. The humeral liner can define a split curvature bearing surface including a plurality of curvature regions including at least a first curvature region having a first curvature and a second curvature region having a second curvature, which can be different than the first curvature. The method can also include mounting a glenoid implant including a glenosphere to a glenoid region of a scapula and positioning the humeral implant such that at least one of the curvature regions operably engages the glenosphere of the glenoid implant.

In at least one example, the method can also include resecting at least a portion of the humerus to provide a humeral mounting surface for receiving the humeral implant, and resecting at least a portion of the scapula to provide a glenoid mounting surface for receiving the glenoid implant. The method can also include positioning a spacer between the humeral liner and the humeral stem.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
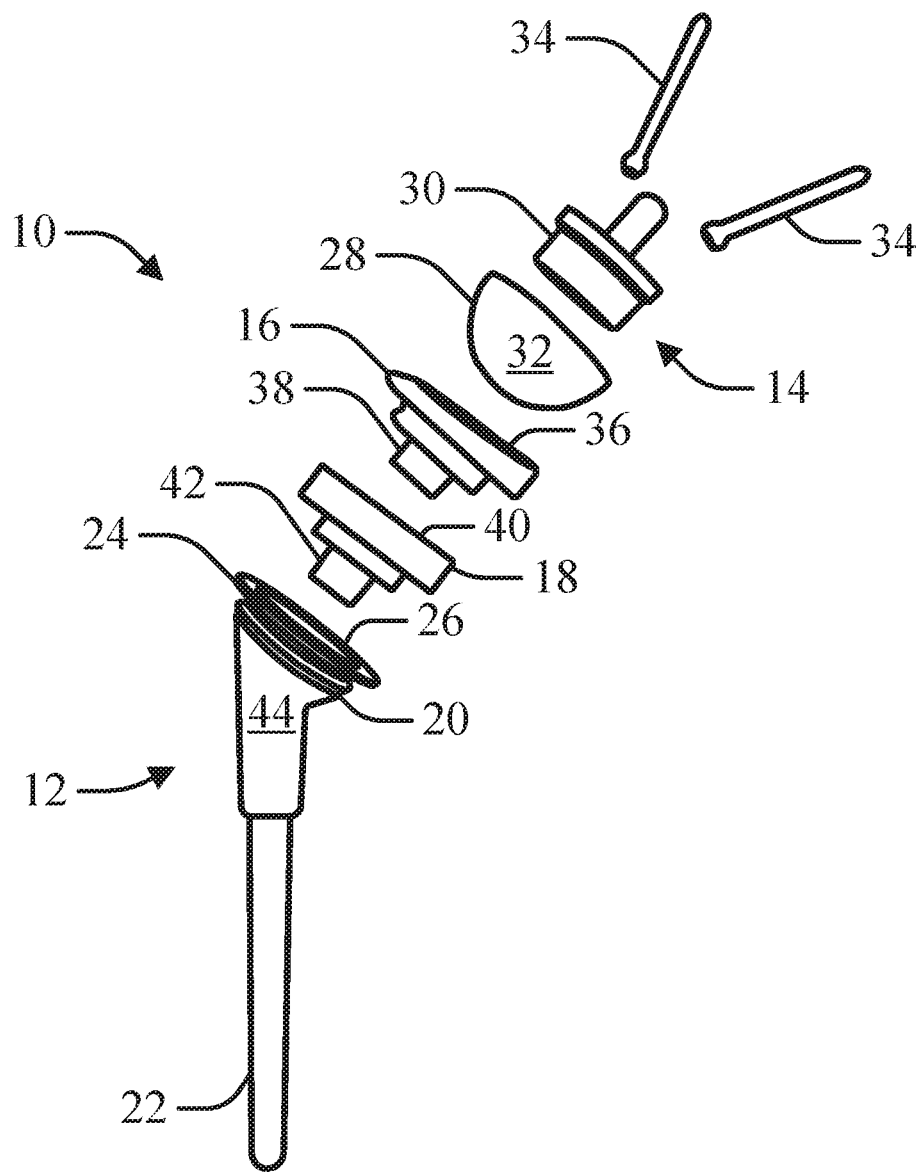
FIG. 1 is an exploded view of a reverse shoulder implant system according to an example of the present disclosure.

As depicted in FIG. 1, a reverse shoulder implant system 10, according to at least one example of the present disclosure, can include a humeral implant 12, a glenoid implant 14 and a humeral liner 16. The humeral implant 12 can be mounted to a humerus, and the glenoid implant 14 can be mounted to the scapula at the glenoid cavity. The humeral liner 16 can be positioned on the humeral implant 12, such as to provide an interface between the humeral implant 12 and the glenoid implant 14. In at least one example, a spacer 18 can be positioned between the humeral implant 12 and the humeral liner 16, such as to change the axial positioning of the humeral liner 16 on the humeral implant 12.

The humeral implant 12 can include an attachment head 20 and a humeral stem 22. The attachment head 20 can define a planar surface 24 and can be configured to operably engage the humeral liner 16 or the spacer 18 such that the humeral liner 16 or the spacer 18 is positioned against the planar surface 24. In at least one example, the attachment head 20 can include a port 26, such as for receiving a shank of the humeral liner 16 or the spacer 18, such as to couple the humeral liner 16 or the spacer 18 to the attachment head 20. As depicted in FIG. 1, the attachment head 20, such as to couple to the spacer 18 or the humeral liner 16, such as with a Morse taper type coupling, but the attachment head 20 can also be configured to be coupled through a screw-in configuration, a flexible tab or detent configuration, or one or more other mechanical coupling arrangements.

The glenoid implant 14 can include a glenosphere 28 and a base plate 30. The glenosphere 28 can comprise an exterior face 32 having a hemispherical shape. In at least one example, the curved exterior face 32 of the glenosphere 28 can have a diameter between about 34 mm to about 46 mm. The base plate 30 can be attached to the glenosphere 28, such as opposite the exterior face 32 of the glenosphere 28. In at least one example, the glenosphere 28 can include a shank, such as can be engaged to a corresponding port defined by the base plate 30. The base plate 30 can be attached to the glenosphere 28 such as through a Morse taper configuration, a screw-in configuration, a flexible tab or detent configuration, or one or more another mechanical arrangement. In at least one example, the glenosphere 28 can be integral to the base plate 30. The base plate 30 can be configured to receive at least one locking screw 34, such as for mounting the base plate 30 to the scapula. In at least one example, the base plate 30 can be configured to receive at least one locking screw cap, such as to fix the positioning of the locking screw 34 within the base plate 30.

The humeral liner 16 can define a split curvature bearing surface 36 on a face of the humeral liner 16 and can include a mounting shank 38 such as extending from an opposite face of the humeral liner 16. The mounting shank 38 can be received within the port 26 of the attachment head 20, such as to mount the humeral liner 26 to the humeral implant 12. In at least one example, the split curvature bearing surface 36 can comprise a biocompatible deformable material, such as including, but not limited to polyethylene. The deformable material can facilitate wearing in or bedding of the split curvature bearing surface 36 such as during prolonged use to improve the fit of the resulting shoulder joint. The deformable material can also be configured to deform or deflect through applied force from the glenosphere 28 such as to further improve the fit between the glenosphere 28 and the split curvature bearing surface 26. In at least one example, the mounting shank 38 can comprise a more rigid material to facilitate improved engagement of the humeral liner 16 to the attachment head 20.

The spacer 18 can include a port 40 on one face and a mounting shank 42 on an opposing face. The port 40 can be configured to receive the mounting shank 38 of the humeral liner 16 or the mounting shank 42 of another spacer 18 to create a spacer liner stack. The mounting shank 42 of the bottommost spacer 18 can be inserted into the port 26 of the attachment head 20, such as to couple the spacer liner stack to the attachment head 20.

A method for implementing the reverse shoulder implant system 10 can include preparing the humerus and the glenoid socket of the scapula; mounting the humeral implant to the humerus and the glenoid implant to the glenoid socket, and slidably engaging the glenosphere 28 to the split curvature bearing surface 36. In at least one example, the glenosphere 28 can wear in or bed the split curvature bearing surface 36 through continued use of the shoulder joint.

The humerus can be prepared by resecting at least a portion of the humeral head to expose the medullary cavity of the humerus. In at least one example, the humeral head region can be resected to provide at least one generally planar surface for cooperating with the attachment head 20 of the humeral implant 12. The glenosphere 28 can be prepared by resecting damaged portions of the scapula adjacent to the glenoid socket. In at least one example, the scapula can be shaped to provide an engagement surface for receiving the base plate 30 and the locking screws 34.

The humeral implant 12 can be mounted by inserting the humeral stem 22 into the medullary cavity of the humerus. The humeral stem 22 can be cemented within the medullary cavity or retained within the humerus by friction. In at least one example, the attachment head 20 can have a textured surface 44 for improving engagement of the attachment head 20 to the humerus. In certain examples, the textured surface can comprise TRABECULAR METAL®. The attachment head 20 can be positioned within the humerus such that the planar surface 24 substantially aligns with the planar or generally planar surfaces of the humerus.

The attachment head 20 can be angled relative to the longitudinal axis of the humeral stem 22, such as to orient the planar surface 24 generally toward the glenoid socket when the humeral stem 22 is inserted into the medullary cavity. The humeral liner 16 can be coupled to the attachment head 20 either directly or stacked with a spacer 18 such that the split curvature planar surface 36 is oriented toward the glenoid socket and at the proper distance.

The base plate 30 can be coupled to the prepared glenoid socket by inserting the locking screws 34 through the base plate 30 and into the scapula. Locking screw caps can be attached, such as to inhibit or prevent adjustment of the locking screws 34 to fix the orientation of the base plate 30 within the glenoid socket. In at least one example, the space provided by the surrounding scapula can be evaluated to determine the appropriate diameter glenosphere 28 for the provided space and joint angle. The selected glenosphere 28 can be coupled to the base plate 30 such that the glenosphere 28 is oriented toward the split curvature planar surface 36.

The humerus can be manipulated to contact the glenosphere 28 with the split curvature planar surface 36. The deltoid muscle can maintain the glenosphere 28 with the split curvature planar surface 36.

Figure 2:
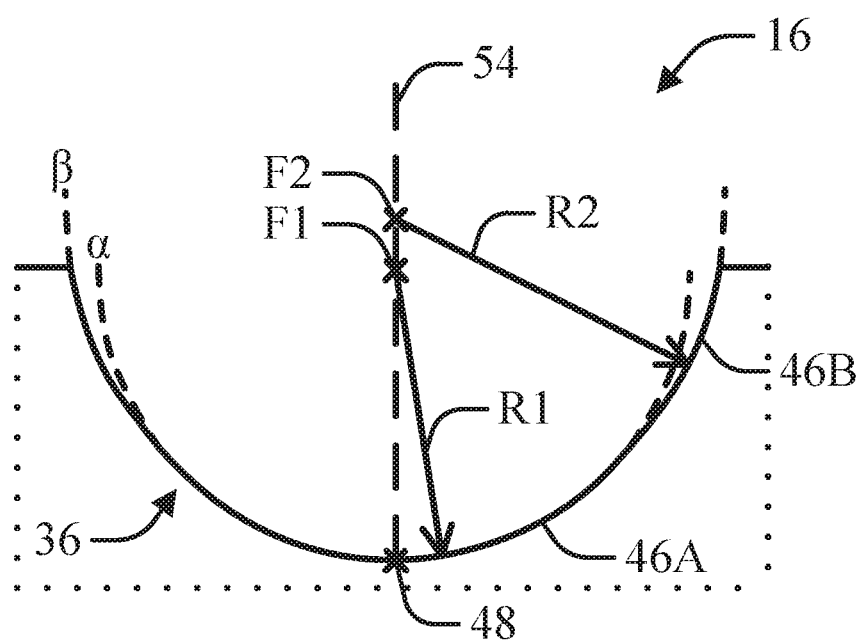
FIG. 2 is a schematic diagram of a humeral liner according to an example of the present disclosure.

As depicted in FIG. 2, the split curvature planar surface 36 can include a plurality of curvature regions 46. As depicted, the split curvature planar surface 36 includes a single split and two curvature regions 46. In certain examples, the split curvature planar surface 36 can include multiple splits and a plurality of curvature regions 46. In at least one example, the plurality of curvature regions 46 can be arranged concentrically about a central apex 48 defined by the split curvature bearing surface 36. In at least one example, one or more of the curvature regions 46 can be offset from the central apex 48 or centered on an axis offset from the central apex 48. The split curvature bearing surface 36 can include at least a first curvature region 46A and a second curvature region 46B. The first curvature region 46A can have a first curvature α defined by a first radius R1 extending from a first focal point F1. Similarly, the second curvature region 46B can have a second curvature β defined by a second radius R2 extending from a second focal point F2. The second curvature β can be the same as or different than the first curvature α. The first focal point F1 and the second focal point F2 can be positioned to intersect a center axis 54 intersecting the central apex 48 of the split curvature bearing surface 36. In at least one example, the first focal point F1 can be positioned closer to the central apex 48 than the second focal point F2.

In at least one example, the difference between the first radius R1 and the second radius R2 can be determined such as to reduce or minimize the difference between the first curvature α and the second curvature β. This arrangement can reduce the likelihood of a significant mismatch between the diameter of the glenosphere 28 and the curvature of the first or second curvature region 46A, 46B. In an example, the difference between the first radius R1 and the second radius R2 can be less than about 30%. In at least one example, the difference between the first radius R1 and the second radius R2 can be less than about 25%. In at least one example, the difference between the first radius R1 and the second radius R2 can be less than about 20%.

Figure 3:
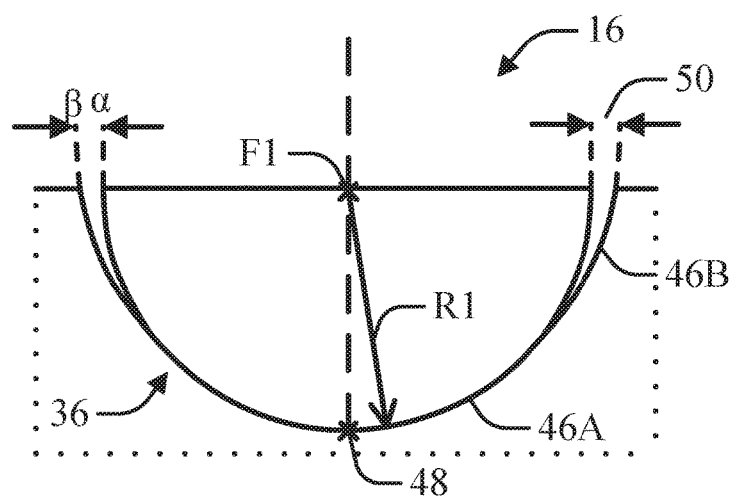
FIG. 3 is a schematic diagram of the humeral liner depicted in FIG. 2 interfacing with a glenosphere having a diameter corresponding to a first curvature region of the humeral liner.

As depicted in FIG. 3, the engagement of a glenosphere 28 having a first diameter that corresponds to the first curvature α slidably engages the first curvature region 46A. In at least one example, the second radius R2 can be greater than the first radius R1 such that the second curvature R is less than the first curvature α. In this arrangement, radial gaps 50 can be created between the curved exterior face 32 of the glenosphere 28 and the second curvature region 46B. In at least one example, the surface area of the first curvature region 46A can provide sufficient depth for the first curvature region 46A to inhibit or prevent from the glenosphere 28 from tracking within the gaps 50. During wearing in or bedding, the glenosphere 28 can wear, deform or deflect the first curvature region 46A such as to further improve seating of the glenosphere 28 within the split curvature bearing surface 36.

Figure 4:
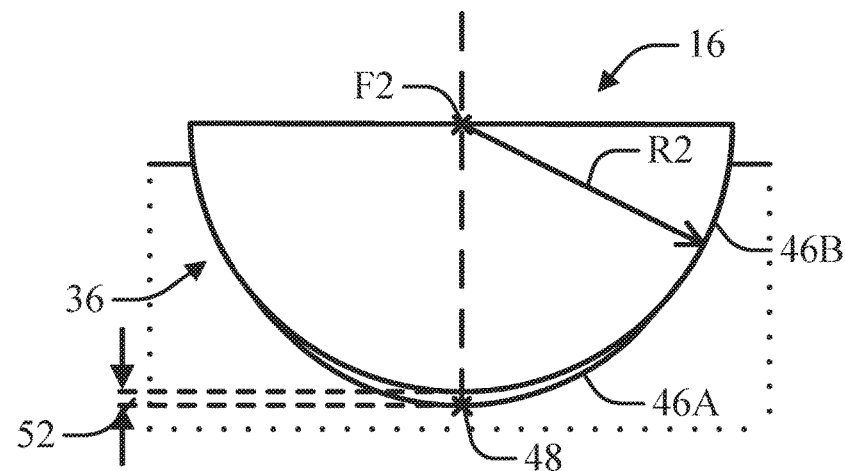
FIG. 4 is a schematic diagram of the humeral liner depicted in FIG. 2 interfacing with a glenosphere having a diameter corresponding to a second curvature region of the humeral liner.

As depicted in FIG. 4, the engagement of a glenosphere 28 having a second diameter that corresponds to the second curvature 3 slidably engages the second curvature region 46B. While the second radius R2 can be greater than the first radius R1, an axial gap 52 is created between the curved exterior face 32 of the glenosphere 28 and the first curvature region 46A. In at least one example, the surface area of the first curvature region 46A is sufficiently small such that the glenosphere 28 cannot track within the axial gap 52. During wearing in or bedding, the glenosphere 28 can wear, deform or deflect the interface between the first curvature region 46A and/or the second curvature region 46B such that the first curvature α approximates the second curvature β, such as to improve seating of the glenosphere 28 within the split curvature bearing surface 36.

Various Notes & Examples

Example 1 can include subject matter, such as a reverse shoulder replacement system 10, comprising: a humeral liner 16 defining a split curvature bearing surface 36. The split curvature bearing surface 36 can include a plurality of curvature regions 46 including at least: a first curvature region 46A having a first curvature α and a second curvature region 46B having a second curvature β.

Example 2 can include, or can optionally be combined with the subject matter of Example 1, to optionally include that the first curvature α can be defined by a first radius R1 extending from a first focal point F1 and that the second curvature β can be defined by a second radius R2 extending from a second focal point F2.

Example 3 can include, or can optionally be combined with the subject matter of Example 1, to optionally include that the first radius R1 is shorter than the second radius R2 such that the second curvature β is shallower than the first curvature α.

Example 4 can include, or can optionally be combined with the subject matter of one or any combination of Examples 2 or 3 to optionally include that the first radius R1 is at least about 75% of the second radius R2.

Example 5 can include, or can optionally be combined with the subject matter of one or any of the preceding Examples to optionally include that the first focal point F1 is a first distance from an apex 48 of the split curvature bearing surface 36 and the second focal point F2 is a second distance from the apex 48. The second distance can be greater than the first distance.

Example 6 can include, or can optionally be combined with the subject matter of one or any of the preceding Examples to optionally include that the plurality of curvature regions 46 can be arranged concentrically such that the second curvature region 46B extends around the first curvature region 46A.

Example 7 can include, or can optionally be combined with the subject matter of one or any of the preceding Examples to optionally include that the humeral liner 16 comprises a biocompatible deformable material.

Example 8 can include, or can optionally be combined with the subject matter of Example 7, to optionally include that the biocompatible deformable material comprises polyethylene.

Example 9 can include, or can optionally be combined with the subject matter of one or any of the preceding Examples to optionally including a humeral implant 12 having a humeral stem 22 insertable into a humerus. The humeral liner 16 can be positioned on an end of the humeral stem. The combination can also include a glenoid implant 14 including a glenosphere 32 and a base plate 30 for receiving at least one fastener 34 for mounting the glenoid implant 14 to a scapula.

Example 10 can include, or can optionally be combined with the subject matter of Example 9, to optionally include a spacer 18 positionable between the humeral liner 16 and the humeral stem 22.

Example 11 can include subject matter, such as a method that can include inserting a stem 22 of a humeral implant 12 into a humerus and mounting a humeral liner 16 to an end of the stem 22. The humeral liner 16 can define a split curvature bearing surface 36 including a plurality of curvature regions 46. The curvature regions 46 can include at least: a first curvature region 46A having a first curvature α and a second curvature region 46B having a second curvature β. The method can also include mounting a glenoid implant 14 to a glenoid region of a scapula where the glenoid implant 14 includes a glenosphere 32, and positioning the humeral implant 12 such that at least one of the curvature regions 46A, 46B operably engages the glenosphere 32 of the glenoid implant 14.

Example 12 can include, or can optionally be combined with the subject matter of Example 11, to optionally include that the first curvature α can be defined by a first radius R1 extending from a first focal point F1 and that the second curvature β can be defined by a second radius R2 extending from a second focal point F2.

Example 13 can include, or can optionally be combined with the subject matter of Example 12, to optionally include that the first radius R1 is shorter than the second radius R2 such that the second curvature β is shallower than the first curvature α.

Example 14 can include, or can optionally be combined with the subject matter of one or any combination of Examples 12 or 13 to optionally include that the first radius R1 is at least about 75% of the second radius R2.

Example 15 can include, or can optionally be combined with the subject matter of one or any of preceding Examples 11-14 to optionally include that the first focal point F1 is a first distance from an apex 48 of the split curvature bearing surface 36 and the second focal point F2 is a second distance from the apex 48. The second distance can be greater than the first distance.

Example 16 can include, or can optionally be combined with the subject matter of one or any of preceding Examples 11-15 to optionally include that the plurality of curvature regions 46 can be arranged concentrically such that the second curvature region 46B extends around the first curvature region 46A.

Example 17 can include, or can optionally be combined with the subject matter of one or any of preceding Examples 11-16 to optionally include that the humeral liner 16 comprises a biocompatible deformable material.

Example 18 can include, or can optionally be combined with the subject matter of Example 17, to optionally include that the biocompatible deformable material comprises polyethylene.

Example 19 can include, or can optionally be combined with the subject matter of one or any of preceding Examples 11-18 to optionally include resecting at least a portion of the humerus to provide a humeral mounting surface for receiving the humeral implant 12; and resecting at least a portion of the scapula to provide a glenoid mounting surface for receiving the glenoid implant 14.

Example 20 can include, or can optionally be combined with the subject matter of one or any of preceding Examples 11-18 to optionally include positioning a spacer 18 between the humeral liner 16 and the humeral stem 12.

Each of these non-limiting examples can stand on its own or can be combined in any permutation or combination with any one or more of the other examples.

The above-detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B." unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A method for reverse replacement of a shoulder joint, comprising:
    inserting a stem of a humeral implant into a humerus;
    mounting a humeral liner to an end of the stem, wherein the humeral liner defines a split curvature bearing surface including a plurality of curvature regions including at least:
        a first curvature region having a first curvature, and
        a second curvature region having a second curvature different than the first curvature;
    selecting a glenosphere from a plurality of glenospheres including at least one glenosphere having a first curved exterior surface that corresponds to the first curvature and at least one glenosphere having a second curved exterior surface that corresponds to the second curvature; and
    mounting the selected glenosphere to a glenoid region of a scapula.

2. The method of claim 1, wherein the first curvature is defined by a first radius extending from a first focal point positioned a first distance from an apex;
    wherein the second curvature is defined by a second radius extending from a second focal point positioned a second distance from the apex.

3. The method of claim 2, wherein the first radius is shorter than the second radius such that the second curvature is shallower than the first curvature.

4. The method of claim 2, wherein the first radius is at least about 75% of the second radius.

5. The method of claim 1, wherein a first focal point is a first distance from an apex of the split curvature bearing surface and a second focal point is a second distance from the apex;
    wherein the second distance is greater than the first distance.

6. The method of claim 1, wherein the plurality of curvature regions are arranged concentrically such that the second curvature region extends around the first curvature region.

7. The method of claim 1, wherein the humeral liner comprises a biocompatible deformable material.

8. The method of claim 7, wherein the biocompatible deformable material comprises polyethylene.

9. The method of claim 1, further comprising:
    resecting at least a portion of the humerus to provide a humeral mounting surface for receiving the humeral implant; and
    resecting at least a portion of the scapula to provide a glenoid mounting surface for receiving the selected glenosphere.

10. The method of claim 1, further comprising:
    positioning a spacer between the humeral liner and the humeral stem.

11. A method for reverse replacement of a shoulder joint, comprising:
    mounting a humeral implant to a humerus;
    securing a humeral liner to the humeral implant, wherein the humeral liner defines a split curvature bearing surface including a plurality of curvature regions including at least:
        a first curvature region having a first curvature, and
        a second curvature region having a second curvature different than the first curvature;
    selecting a glenoid implant from a plurality of glenoid implants including at least one glenoid implant having a first curved exterior surface that matches the first curvature of the first curvature region and at least one glenoid implant having a second curved exterior surface that matches the second curvature of the second curvature region; and
    mounting the selected glenoid implant to a glenoid region of a scapula.

12. The method of claim 11, further comprising:
    positioning the selected glenoid implant relative to the humeral liner such that the selected glenoid implant operably engages either the first curvature region or the second curvature region.

13. The method of claim 12, further comprising:
    inserting a spacer between the humeral liner and a stem of the humeral implant.

14. The method of claim 11, wherein the plurality of curvature regions are arranged concentrically such that the second curvature region extends around the first curvature region.

15. The method of claim 11, wherein the first curvature is defined by a first radius extending from a first focal point, and wherein the second curvature is defined by a second radius extending from a second focal point.

16. The method of claim 15, wherein the first radius is shorter than the second radius such that the second curvature is shallower than the first curvature.

17. A method for reverse replacement of a shoulder joint, comprising:
    mounting a humeral implant to a humerus;

securing a humeral liner to the humeral implant, wherein the humeral liner defines a split curvature bearing surface including a plurality of curvature regions including at least:
- a first curvature region defined by a first curvature, and
- a second curvature region defined by a second curvature different than the first curvature;

selecting a glenoid implant from a plurality of glenoid implants including at least one glenoid implant having a first glenoid bearing surface defined by a first diameter that corresponds to the first curvature and at least one glenoid implant having a second glenoid bearing surface defined by a second diameter that corresponds to the second curvature; and mounting the selected glenoid implant to a glenoid region of a scapula.

18. The method of claim 17, further comprising:
positioning the selected glenoid implant relative to the humeral liner such that the selected glenoid implant operably engages either the first curvature region or the second curvature region.

19. The method of claim 17, further comprising:
preparing the humerus for receipt of the humeral implant; and
preparing the scapula for receipt of the selected glenoid implant.

20. The method of claim 17, wherein the first curvature region is defined by a first radius that extends from a first focal point and the second curvature region is defined by a second radius that extends from a second focal point, the first and second focal points disposed along a longitudinal axis that intersects a central apex of the humeral liner.

* * * * *